US012135301B2

United States Patent
Ainger et al.

(10) Patent No.: US 12,135,301 B2
(45) Date of Patent: Nov. 5, 2024

(54) POINT OF CARE SEPSIS ASSAY DEVICE AND METHOD

(71) Applicant: FREQUASENSE LIMITED, Liverpool (GB)

(72) Inventors: Phill Ainger, Liverpool (GB); Colin Downey, Liverpool (GB); David George, Liverpool (GB)

(73) Assignee: FREQUASENSE LIMITED, Liverpool (GB)

( * ) Notice: Subject to any disclaimer, the term of this patent is extended or adjusted under 35 U.S.C. 154(b) by 0 days.

(21) Appl. No.: 17/913,029

(22) PCT Filed: Mar. 22, 2021

(86) PCT No.: PCT/GB2021/050698
§ 371 (c)(1),
(2) Date: Sep. 20, 2022

(87) PCT Pub. No.: WO2021/186198
PCT Pub. Date: Sep. 23, 2021

(65) Prior Publication Data
US 2023/0146070 A1    May 11, 2023

(30) Foreign Application Priority Data
Mar. 20, 2020    (GB) ...................... 2004047

(51) Int. Cl.
*G01R 27/28*    (2006.01)
*B01L 3/00*    (2006.01)
(Continued)

(52) U.S. Cl.
CPC ........ *G01N 27/02* (2013.01); *B01L 3/502715* (2013.01); *G01N 33/48707* (2013.01);
(Continued)

(58) Field of Classification Search
CPC ............. G01N 33/48707; G01N 33/49; G01N 33/48735; G01N 33/5438; G01N 33/5091;
(Continued)

(56) References Cited

U.S. PATENT DOCUMENTS

| 8,635,028 B2 * | 1/2014 | Sengupta | ........... G01N 33/5438 |
| | | | 702/19 |
| 10,012,645 B2 * | 7/2018 | Kaushik | ............. G01N 27/3278 |

(Continued)

FOREIGN PATENT DOCUMENTS

| EP | 2395353 A1 | 12/2011 |
| WO | 03073099 A1 | 9/2003 |
| WO | 2017132132 A1 | 8/2017 |

OTHER PUBLICATIONS

International Search Report and Written Opinion mailed on Jun. 9, 2021, in corresponding to International Application No. PCT/GB2021/050698; 11 pages.
(Continued)

*Primary Examiner* — Thang X Le
(74) *Attorney, Agent, or Firm* — Maier & Maier, PLLC

(57) ABSTRACT

The present invention relates generally to the field of disposable assay test devices, particularly for use in point-of-care assays. The invention further relates to the use of such devices, including kits comprising such devices, to facilitate the accurate measurement of the levels of sepsis in the blood using electronic measurements.

20 Claims, 2 Drawing Sheets

Figure 1A:
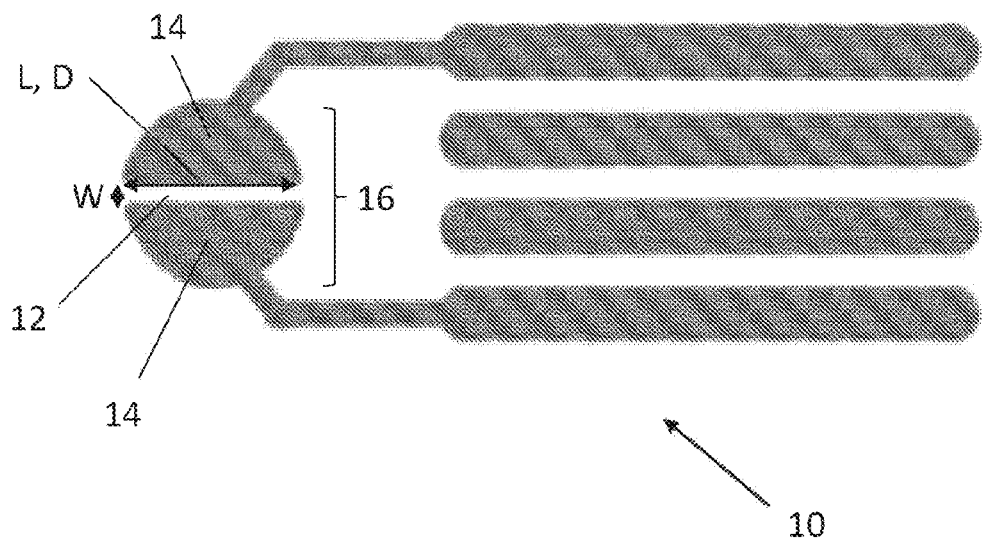

(51) Int. Cl.
*G01N 27/02* (2006.01)
*G01N 33/487* (2006.01)
*G01N 33/49* (2006.01)

(52) U.S. Cl.
CPC ...... *G01N 33/49* (2013.01); *B01L 2300/0645* (2013.01); *B01L 2300/16* (2013.01)

(58) Field of Classification Search
CPC ............. G01N 33/54373; G01N 27/02; G01N 27/026; G01N 27/3278
See application file for complete search history.

(56) References Cited

U.S. PATENT DOCUMENTS

| | | | | |
|---|---|---|---|---|
| 2005/0059105 | A1* | 3/2005 | Alocilja | G01N 33/569 435/287.1 |
| 2007/0158189 | A1* | 7/2007 | Yang | G01N 33/48785 204/403.02 |
| 2008/0176334 | A1* | 7/2008 | Baranov | G01N 33/532 436/80 |
| 2011/0024309 | A1* | 2/2011 | Lee | G01N 33/54373 205/792 |
| 2013/0295556 | A1* | 11/2013 | Schmera | G01N 33/48735 435/5 |

OTHER PUBLICATIONS

Search Report dated Jul. 29, 2020, in corresponding to GB Application No. 2004047.3; 1 page.

Morse, "Electrical Bioimpedance as a detection tool for internal hemorrhaging and blood aggregation", A thesis submitted to the Faculty of Graduate and Postdoctoral Studies in partial fulfillment of the requirements for the MASc degree in Biomedical Engineering, Jan. 1, 2014, 99 pages.

Sea Bird Scientific, "Instructions for Care and Cleaning of Conductivity Cells", Jun. 1, 2016, 6 pages.

* cited by examiner

POINT OF CARE SEPSIS ASSAY DEVICE AND METHOD

FIELD OF THE INVENTION

The present invention relates generally to the field of disposable assay test devices, particularly for use in point-of-care assays. The invention further relates to the use of such devices, including kits comprising such devices, to facilitate the accurate measurement of the levels of sepsis in the blood.

BACKGROUND

Sepsis, or blood poisoning, is a potentially deadly medical condition characterized by a whole-body inflammatory state triggered by an infection. Sepsis is a vast clinical entity that takes many forms. The pathophysiology of a host response to infection is complex and the signs and symptoms of systemic inflammation may have an infectious or non-infectious etiology and are not specific. In response to microbes or viruses in the blood, urine, lungs, skin, or other tissues, the body may develop a systemic inflammatory response, eventually resulting in organ dysfunction and death. Patients with systemic infection are often difficult to distinguish from patients with similar clinical signs and laboratory findings without infection. Infection has multiple causes including that caused by bacterium, fungi, parasites and viruses.

Sepsis can be identified by the presence of pathogenic organisms in the bloodstream. Sepsis is usually treated with intravenous fluids and antibiotics. Sepsis can be the result of the presence of more than one type of organism, and there it is important to both identify the presence of the infection as early as possible before severe symptoms occur, and to regularly monitor blood samples from the patient during treatment to ensure the antibiotics are effective and the patient does not suffer from further infections.

Bacteriological evidence of infection may not develop at the same time as clinical signs of distress. Further, it requires time to grow a culture of organism from a blood sample to confirm the presence of infective bacteria and the results may be incorrect due to contamination, etc. As used herein, severe infection may include a diagnosis of sepsis, severe sepsis, septicaemia, and septic shock as well as disseminated intravascular coagulation ("DIC"). Also included in the definition of infection is systemic inflammatory response syndrome "SIRS" although it may have infectious as well as non-infectious origin (both of which are encompassed herein). SIRS may exhibit or develop into systemic inflammation that ultimately leads to multiple organ dysfunction syndrome. Patients with SIRS may develop the syndrome from infection, trauma, burns, pancreatitis, etc.

Blood poisoning correlates with hemostatic dysfunction and may be defined as an error in coagulation. For both DIC and sepsis, there is increasing recognition of common and overlapping pathophysiological pathways that link inflammation and coagulation. The recent therapeutic success of recombinant human activated protein C (APC) in severe sepsis especially after a myriad of unsuccessful strategies would support this further. APC suppresses thrombin generation via the inactivation of coagulation co-factors, Va and VIIIa and is also thought to have anti-inflammatory properties.

There is a continuing need to find early indicators or markers of infection, SIRS and hemostatic dysfunction due to lack of specificity of current methods of diagnosis. An early diagnosis may greatly increase recovery of the patient and reduce the morbidity and mortality rates associated with this population. Further a diagnostic marker or test to monitor the efficacy of treatment of the host response to infection, SIRS and hemostatic dysfunction is needed as well.

The time dependent measurement profiles of coagulation screening assays have been associated with predicting congenital, acquired imbalances and hemostatic dysfunction as described in Givens et al. WO 96/41291 and Toh et al. WO 00/46603. Once such profile is that of an activated partial thromboplastin time ("APTT") assay having a decrease in plasma light transmittance before clot formation, now commonly referred to as a biphasic waveform (also referred to herein as BPW). This BPW has been associated with critically ill patients having DIC which is common in many primary diseases including sepsis. Measurement of the biphasic waveform on coagulation instruments offers a simple and rapid test for early diagnosis of hemostatic dysfunction, including DIC.

As described in WO 01/96864 (Dec. 20, 2001), a calcium-dependent complex between C reactive protein (CRP) and lipoprotein (particularly very low density lipoprotein (VLDL)) has been identified as the molecular mechanism underlying the biphasic waveform. The complex may be used to identify patients with sepsis, SIRS and septicaemia in addition to patients with other hemostatic dysfunction that can lead to bleeding or thrombosis including DIC. Further, WO 01/96864 describes detecting the complex by a clotting assay, latex agglutination or gold sol assay, and immunoassay whereby the precipitate is formed prior to or in the absence of clot formation, depending on the reagent used.

Very low-density lipoprotein (VLDL), is a type of lipoprotein made by the liver. VLDL is assembled in the liver from triglycerides, cholesterol, and apolipoproteins. VLDL particles have a diameter of 30-80 nm. Very low-density lipoproteins transport endogenous triglycerides, phospholipids, cholesterol, and cholesteryl esters and thereby function as the body's internal transport mechanism for lipids. Changes in the profiles of triglycerides and VLDL in the blood stream are indicative of sepsis in patients. Sepsis has been found to cause in increase in the rate of VLDL production. Elevated plasma lipid levels are known to be an early hallmark of sepsis. This increase in circulating lipids is mainly the result of rapid accumulation of triglycerides (TGs) within VLDLs. The accumulation of VLDL particles in the plasma is attributable to disturbances in their metabolism, including increased production in the liver and reduced peripheral clearance in the bloodstream by lipoprotein lipase (LPL).

C-reactive protein (CRP) is one of the common test parameters used in clinical practice, to assess, diagnose, and prognose inflammation. C-reactive protein (CRP), an acute phase protein belonging to pentraxin family of proteins, increases 1000-fold or more in concentration in blood during the occurrence of an injury, inflammation or tissue death. CRP is known to be involved in conjugation of pathogens to induce their destruction by complement system and is also studied as a marker of inflammation, disease activity and a diagnostic adjunct. The complex between C reactive protein (CRP) and lipoprotein (particularly very low density lipoprotein (VLDL)) is formed and precipitated in the presence of calcium or other divalent metal ions, thus the level of CRP-VLDL complex formation is therefore an assay for the level of CRP in the sample.

WO2014/096856 describes a method and disposable single use device for detecting sepsis using optical measurements. The device contains a transparent window to measure the change in turbidity in a sample of blood plasma. However the use of optical measurements requires certain hardware in the form of light sources and detectors to measure transmitted light at defined wavelengths, and is therefore somewhat limited in point of care applications.

While measuring the biphasic waveform to determine the levels of the CRP-lipoprotein complex provide advances in the early diagnosis of different kinds of severe infection and haemostatic dysfunction (including DIC and sepsis), there is a continued need to simplify the assays further, and therefore a simplified point of care version of the assay which can be carried out using a small amount of blood and gives an immediate electronic read out is highly desirable.

Whilst electrode based assays are well known, prior art assays rely on specific immobilisation of material to the electrodes, and are thus complex and expensive to implement. Contrary to prior art electrode assays, for example requiring tethered anti-CRP antibodies and affinity binding and washing, the assays herein are performed simply by measuring the properties of the reagents in the solutions to which the electrodes are exposed rather than requiring material to be specifically tethered to or immobilised on the electrodes.

SUMMARY OF THE INVENTION

Disclosed herein is an electronic assay for the detection of sepsis in a sample. The assay relies on measuring an electronic signal in the form of an inductive reactance value of the sample. The electrode geometry allows measurement of inductive reactance at a frequency of 70-90 KHz, which is specific for particles of VLDL. The presence of sepsis can be clearly seen as samples with sepsis have VLDL particles which show an increase in inductive reactance, followed by a rapid fall, and therefore deviate from the sine wave of the alternating current. Samples where sepsis is absent have VLDL particles which do not deviate from the expected sine wave. Changes in the sine wave at the resonance frequency are therefore characteristic for the changes in the VLDL particles indicative of sepsis.

Inductive reactance refers to the opposition to a changing current flow. This impedance is measured in ohms, just like resistance. In inductors, voltage leads current by 90 degrees. Reactance is used to compute amplitude and phase changes of sinusoidal alternating current going through a circuit element, and is thus plotted as a sine wave caused by the alternating current.

The inventors herein have appreciated that the VLDL and/or CRP-VLDL lipoprotein complex in solution can be directly characterised, without requiring material to be specifically tethered to or immobilised on the electrodes. By monitoring the inductive reactance via the sinusoidal alternating current the properties of the VLDL and/or CRP-VLDL lipoprotein complex can be monitored by measuring at the frequency where the VLDL particles resonate. By characterising the changes caused by the VLDL particles, a rapid determination of sepsis can be obtained.

Disclosed herein is an electronic sensor for measuring samples to determine the presence of sepsis. Disclosed is an assay device configured to detect sepsis by measuring very low density lipoprotein (VLDL) in a sample of whole blood, plasma or serum, the device comprising an inlet configured to receive a whole blood or blood plasma sample, wherein the inlet is in fluid communication with the electrodes of electronic sensor which is part of a first electronic circuit, wherein the electronic sensor measures the inductive reactance of the VLDL in the sample at a resonance frequency of 70-90 kHz.

Also disclosed herein is an assay device configured to detect sepsis by measuring the inductive reactance of a sample of whole blood, plasma or serum, wherein the device comprises a first electrode and a second electrode separated by a gap, wherein the gap is in fluid communication with an inlet configured to receive the sample and wherein the device is configured such that any VLDL in the sample in the gap resonates at a frequency of 70-90 kHz when an alternating electric field is applied across the first and second electrode.

In some embodiments, the first and second electrodes form part of an electronic circuit comprising an electronic sensor. In some embodiments, the electrodes may be the electronic sensor.

The VLDL or CRP-VLDL lipoprotein complex is measured without being tethered to or immobilised on the electrode. The assay requires no binding or washing steps, the sample is simply applied and directly measured thereafter. No external reagents are required to be added to the sample. No divalent cations are required, there are no additional reagents for coagulation. The electrodes and/or electronic sensor are simply measuring the inductive reactance in the sample at a particular resonance frequency. The frequency being measured is determined by the dimensions of the electrodes. The assay measures properties of the solution, rather than the amount of material bound to the electrodes. The electrodes do not require modification such as to allow any covalent attachment of biomolecules, although the electrodes can be modified such as for example to assist in preventing material sticking or for improved stability.

By measuring the inductive reactance of a sample at the resonance frequency for VLDL particles, the VLDL can be characterised. Samples having sepsis show a change in discharge potential across the sensor, which is reflected in a deviation from the sine wave of the alternating current.

Alternatively, or in addition, samples having sepsis show a change in discharge potential across the electrodes, which is reflected in a deviation from the sine wave of the alternating current.

The VLDL particles in the sample can be unbound in free solution, or can be part of a CRP-lipoprotein complex.

Where the VLDL particles become part of a complex, the resonance frequency of the complex can also be used. Thus the inductive reactance of the sample can also be measured on a second sensor at a resonance frequency of 30-60 kHz. Alternatively, or in addition, the inductive reactance of the sample can also be measured in a gap between a second sensor formed from a third and fourth electrode at a resonance frequency of 30-60 kHz. The geometry of the electrodes must be altered in ordered to measure inductive reactance of the sample at the second frequency, thus the device requires two sets of electrodes in order to measure two frequencies.

The electrodes can be semi-circular. The electrodes can be etched from a circle by cutting a gap across the diameter (D) of the circle. Each electrode pair can be etched from a circle of 2 to 4 millimetres (mm) in diameter (D). The gap between the electrodes can be 150 µm to 200 µm in width (W). In some embodiments, the height (H) of the gap may be 2 to 10 microns.

The volume of the sample between the electrodes should be controlled by having a fixed height (H) to the gap. The width (W) being the gap between the electrodes and the length (L) being the length of the electrodes (i.e. the diameter (D) of the circle where the electrodes are circular). The volume of the solution is thus controlled by the dimension of the electrodes.

The sensors can be fabricated from inert electrically conducting materials. The sensors can be for example gold, silver or palladium. In some embodiments, specifically, the electrodes are gold. In some embodiments specifically, the electrodes are silver. The electrodes can be in the form of in-line or opposed electrodes.

The sample can be whole blood. The sample can be blood plasma. The sample can be blood serum. The device can have an integral filter to remove cellular material. The filter may be located between the inlet and the gap. The filter may be located within the fluid channel between the inlet and the gap. Alternatively the blood can be filtered before entering the device. Alternatively the whole blood can be measured directly. The volume of the sample applied to the device can be 10-20 microlitres (μl).

The sensor can be coated with a dried material containing a surfactant, for example Triton. In order to provide a uniform dried layer, the device can be fabricated in the presence of alcohol and a degreaser to form the dry layer. Disclosed is a method of fabricating the device as disclosed herein, wherein the surfactant is dried onto the surface in the presence of alcohol and a degreaser to form the dry layer. The alcohol can be ethanol.

Also disclosed is a method of detecting sepsis using the device as described herein, wherein the method comprises:
adding a whole blood, blood plasma or blood serum sample to the device via the inlet; generating a resonance signal across the sample at 70-90 kHz once the sample has reached the sensors; and
using inductive reactance measurements, measuring the VLDL, thereby determining whether sepsis is present.

Also disclosed is a method of detecting sepsis using the device as described herein, wherein the method comprises:
adding a whole blood, plasma or serum sample to the device via the inlet;
generating an alternating electric field across the electrodes once the sample has reached the gap between the electrodes; and
measuring the inductive reactance of the VLDL in the sample at a resonant frequency of 70-90 kHz, thereby determining whether sepsis is present.

After application of the sample, the impedance measurements are continuously recorded for a time period after introduction of the sample. Thus the assay is a real-time measurement rather than a single end-point measurement. The time period of the measurement can be between 1-3 minutes after introduction of the sample. Further inductive reactance measurements can be taken at a second frequency in the region of 30-60 kHz.

FIGURES

FIG. 1A shows an assay device 10 according to the present invention. The sample is introduced into the device via an inlet, not shown. The sample flows into a gap 12 having a defined volume, where the electronic sensor 16 measures the inductive reactance of the sample. The volume of the gap 12 is determined based on the gap height (H), width (W) and length (L) or diameter (D). The geometry of each electrode 14 allows measurement at a resonance frequency of 70-90 kHz, which is specific for measuring the inductive reactance of VLDL particles.

Figure 1B:
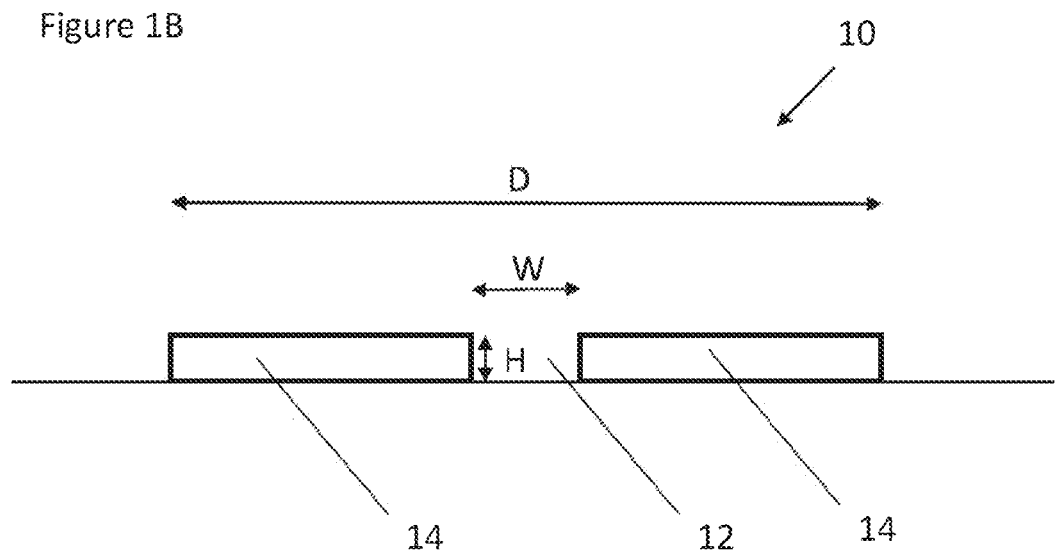

FIG. 1B shows the assay device of FIG. 1A in section.

Figure 2:
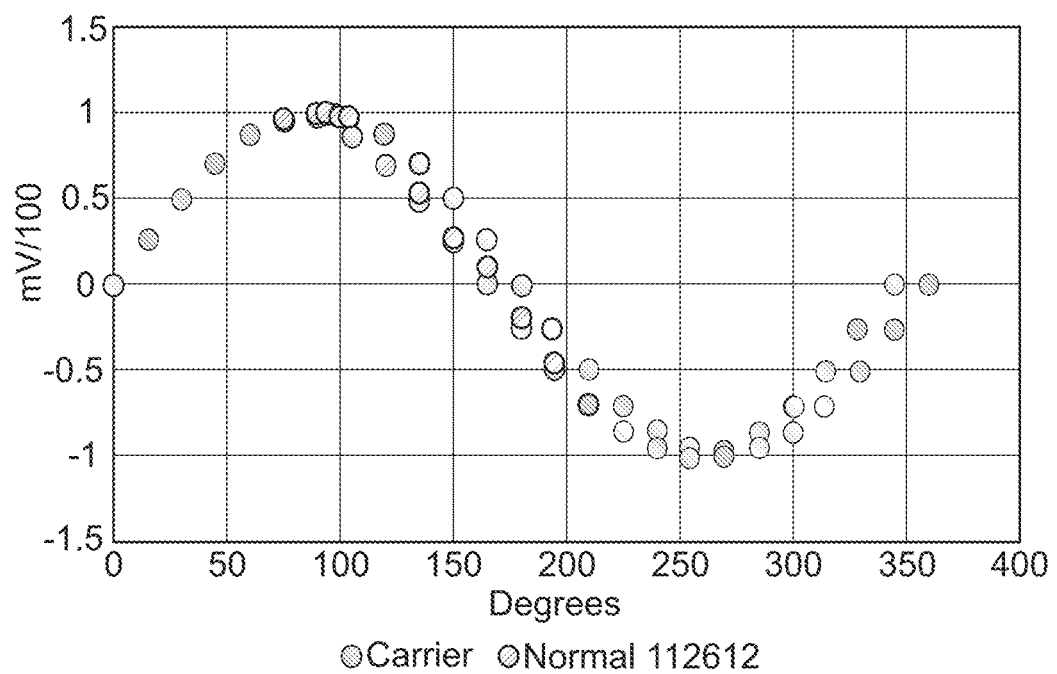
Figure 2:
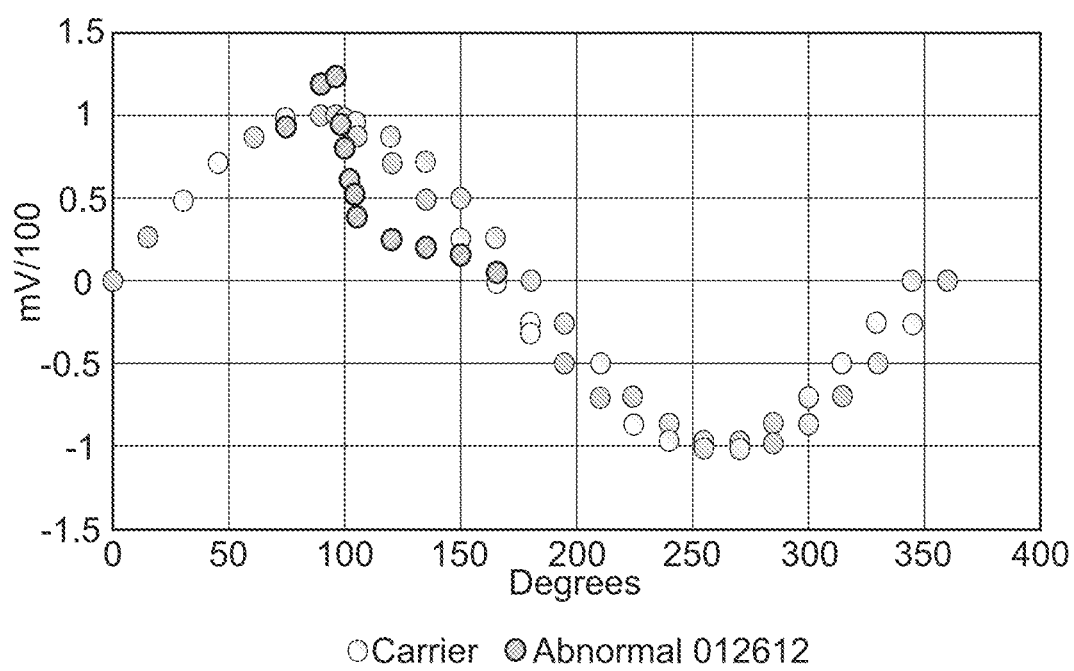

FIG. 2 shows a sample from a patient with sepsis and a normal sample. The normal sample (referred to as 112612) shows a standard sine wave that does not significantly deviate from the carrier. Thus the VLDL is 'normal'. The lower trace is from an 'abnormal sample where the patient has sepsis (referred to as Abnormal 022612). The sample shows an increase at the top of the sine wave followed by a rapid decrease. The difference is caused by the properties of the VLDL, and is characteristic for all samples with sepsis.

DETAILED DESCRIPTION

Disclosed herein is an electronic assay for the detection of sepsis in a sample. The assay relies on measuring an electronic signal in the form of an inductive reactance value of the sample. The electrode geometry allows measurement of inductive reactance at a frequency of 70-90 kHz, which is specific for particles of VLDL. The presence of sepsis can be clearly seen as samples with sepsis have VLDL particles which show an increase in inductive reactance, followed by a rapid fall, and therefore deviate from the sine wave of the alternating current. Samples where sepsis is absent have VLDL particles which do not deviate from the expected sine wave.

The inventors herein have appreciated that the VLDL and/or CRP-VLDL lipoprotein complex in solution can be directly characterised, without requiring material to be specifically tethered to or immobilised on the electrodes. By monitoring the inductive reactance via the sinusoidal alternating current the properties of the VLDL and/or CRP-VLDL lipoprotein complex can be monitored by measuring at the frequency where the VLDL particles resonate. By characterising the changes caused by the VLDL particles, a rapid determination of sepsis can be obtained.

The sensor works by applying a fixed frequency sine wave between the anode and cathode of the sensor and measuring the inductive reactance. The anode may be the first electrode and the cathode may be the second electrode. In order to measure the VLDL particles, the frequency can be in the range of 70-90 kHz, for example around 85 kHz.

Accuracy of the assay can be improved by taking measurements at further additional frequencies. For example, the assay device may further comprise a second sensor formed by a third electrode and a fourth electrode separated by the gap, wherein the device is configured such that the VLDL in the sample in the gap resonates at a frequency of 30-60 kHz when an alternating electric field is applied across the third and fourth electrode. The VLDL can be part of a CRP-VLDL lipoprotein complex. Each CRP molecule can bind multiple lipoprotein molecules. This change in molecular mass of the complex alters the resonance frequency. Therefore taking measurements at lower frequencies can measure the CRP complex with multiple VLDL particles.

Thus for example a range of 30-60 kHz can be used in addition. Specifically a frequency of around 38 kHz. In addition a third frequency of 15-20 kHz can be used, for example around 18 kHz. The variation in frequency allows different molecular weight multi-VLDL complexes to be detected.

The device is configured to detect sepsis by measuring VLDL or the complex between C reactive protein (CRP) and VLDL in a sample of whole blood, plasma or serum. The VLDL is measured without being tethered to or immobilised on the electrode. For example, the inductive reactance of the VLDL is measured without the VLDL being tethered to or immobilised on the electrodes. The assay requires no binding or washing steps, the sample is simply applied and directly measured thereafter. The electrodes are measuring properties of the solution to which they are exposed, rather than the amount of bound material. The electrodes do not require modification such as to allow any covalent attachment of biomolecules, although the electrodes can be modified such as for example to assist in preventing material sticking or for improved stability.

The invention also includes a reader device instrument for measuring the inductive reactance in the sample. The reader instrument is configured to hold the electrode cartridge and supply power across the electrodes, and to measure the change in impedance of the sample over time. The combined cartridge and reader device may be used to measure sepsis.

Inductive reactance refers to the opposition to a changing current flow. This impedance is measured in ohms, just like resistance. In inductors, voltage leads current by 90 degrees. Reactance is used to compute amplitude and phase changes of sinusoidal alternating current going through a circuit element, and is thus plotted as a sine wave caused by the alternating current. Electrical impedance is the measure of the opposition that a circuit presents to a current when a voltage is applied. Impedance extends the concept of resistance to AC circuits, and possesses both magnitude and phase, unlike resistance, which has only magnitude. Electrochemical impedance is usually measured by applying an AC potential to an electrochemical cell and then measuring the current through the cell. Thus the level of impedance is a property of the solution between a pair of electrodes, and can be measured by supplying an AC potential at an electrode and measuring the current flow across the electrode gap. Alternatively, or in addition, the level of impedance can be measured by supplying an alternating electric field across a pair of electrodes and measuring the current flow across the gap between the electrodes.

Substances in the sample resonate at different frequencies, and therefore by measuring the impedance at their particular resonance frequencies, the properties of biomolecular species present in the solution between the electrodes can be determined. The properties of the VLDL particles in a sample with sepsis are different due to changes in the amount of triglycerides. Therefore the VLDL in samples with sepsis show different properties when resonated at the resonant frequency.

Patient samples showing sepsis, the sine wave profiles as an increase, followed by a rapid fall. A normal VLDL sample profiles as a standard sine wave.

Electrode Designs

The depth of commercially available electrodes may determine the height (H) of the gap. For example, commercially available electrodes may have a depth of 2-10 microns ($\mu m$). consequently, the height (H) of the gap may be 2-10 microns ($\mu m$).

Exemplary electrode designs are shown as etched onto sheets of gold. Laser ablation allows the gold to be selectively removed. The typical thickness of commercially available gold sheets can be a 3 micron depth of sputtered gold, although any typical depth, for example 2-10 microns ($\mu m$) can be used.

Exemplary dimensions are described below:

The electrodes are optionally designed as circles with a gap cut across the middle, thereby making two opposing semi-circles. The diameter (D) of the circle can be 2-7 mm, optionally 3-5 mm. The width (W) of the gap can be 50-400 microns, optionally 150 microns ($\mu m$). Thus for example the length (L) of the gap can be 2-7 mm, the width (W) being 150-200 $\mu m$ and the height (H) 2-10 $\mu m$.

For example the circles can be 3 mm in diameter (D). The width (W) of the etched gap can be 150 micrometers (0.15 mm). Thus the area of the gap is 3*0.15 (0.45 mm$^2$). The area of gold pre-etching is $\pi*1.5*1.5=7.1$ mm$^2$. Thus making the area of etched/remaining=7.1/0.45=15.7.

If the depth of the film is 3 $\mu m$, the volume of liquid in the region defined by the electrode is $3000*150*3=1.3\times10^6$ $\mu m^3$. Alternatively, or in addition, if the height of the gap is 3 $\mu m$, the volume of sample in the gap may be $3000*150*3=1.3\times10^6$ $\mu m^3$.

Once prepared the etched gold layers are bonded to a planar substrate in order to seal the gap. The dimensions of the gap are therefore defined by the diameter of the circle, the width/gap between the electrodes and the thickness of the gold layer.

The electrodes are connected to standard commercially available electronic circuit readers, such as for example https://www.redpitaya.com/. The sample is added and readings taken over time in order to measure the change of signal between the electrodes.

In order to measure the VLDL, readings are taken with a positive dc offset of 0.45 V and a frequency of 85 kHz. Each abnormal sample displays a positive nib followed by a rapidly falling edge. The normal follows the sine wave of the current. The abnormal profile is due to the changes in the properties of the VLDL, which are characteristic for abnormal VLDL, and are indicative of sepsis in the sample (See FIG. 2).

The invention claimed is:

1. An assay device configured to detect sepsis by measuring an electrical signal in a form of an inductive reactance of a sample of whole blood, plasma or serum, the device comprises a first electrode and a second electrode separated by a gap, wherein the gap is in fluid communication with an inlet configured to receive the sample and the first and second electrodes are configured to measure any very low density lipoprotein (VLDL) in the sample in the gap resonating at a frequency of 70-90 kHz when an alternating electric field is applied across the first and second electrodes.

2. The device according to claim 1, wherein the VLDL is characterised by a change in discharge potential across the electrodes.

3. The assay device according to claim 1, wherein the VLDL is part of a CRP-lipoprotein complex.

4. The assay device according to claim 1, wherein the inductive reactance of the VLDL is measured without the VLDL being tethered to or immobilised on the electrodes.

5. The assay device according to claim 1, wherein the resonance frequency is 85 kHz.

6. The assay device according to claim 1, further comprising a third electrode and a fourth electrode separated by a gap, wherein the third and fourth electrodes are configured to measure VLDL in the sample in the gap resonates at a frequency of 30-60 kHz when an alternating electric field is applied across the third and fourth electrode.

7. The assay device according to claim 1, wherein each electrode is semi-circular.

8. The assay device according to claim 1, wherein each electrode is etched from a circle of 2 to 4 mm in diameter (D).

9. The assay device according to claim 1, wherein each electrode is etched from a circle by inserting the gap across the diameter of the circle.

10. The assay device according to any of claim 9, wherein the gap is 150 $\mu m$ to 200 $\mu m$ in width (W).

11. The device according to claim 9, wherein the height (H) of the gap is 2 to 10 microns.

12. The device according to claim 1, wherein the electrodes are gold, silver or palladium.

13. The device according to claim 1, wherein the device is configured to receive 10-20 microlitres (µl) of the sample.

14. The device according to claim 1, wherein the electrodes are coated with a dried material containing a surfactant, for example Triton.

15. The device according to claim 1, wherein the electrodes are in-line or opposed electrodes.

16. A method of detecting sepsis using the device according to claim 1, wherein the method comprises:
   adding a whole blood, plasma or serum sample to the device via the inlet;
   generating an alternating electric field across the electrodes once the sample has reached the gap between the electrodes; and
   measuring the inductive reactance of the VLDL in the sample at a resonant frequency of 70-90 kHz, thereby determining whether sepsis is present.

17. The method according to claim 16 wherein inductive reactance measurements are continuously recorded for a time period of between 1 and 3 minutes after introduction of the sample.

18. The method according to claim 16, wherein further inductive reactance measurements of the VLDL in the sample are taken at a second resonant frequency in the region of 30-60 kHz.

19. A method of fabricating the device according to claim 1, wherein a surfactant is dried onto the surface of each electrode in the presence of alcohol and a degreaser to form a dry layer.

20. The assay device according to claim 6, wherein each electrode is etched from a circle of 2 to 4 mm in diameter (D).

* * * * *